US008067201B2

(12) United States Patent
Morin et al.

(10) Patent No.: US 8,067,201 B2
(45) Date of Patent: Nov. 29, 2011

(54) METHODS FOR PROTEIN REFOLDING

(75) Inventors: Paul Morin, Pennington, NJ (US); Zheng Lin, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/763,168

(22) Filed: Apr. 19, 2010

(65) Prior Publication Data

US 2010/0273216 A1  Oct. 28, 2010

Related U.S. Application Data

(60) Provisional application No. 61/212,990, filed on Apr. 17, 2009.

(51) Int. Cl.
*C12P 21/06* (2006.01)
*C12N 9/00* (2006.01)
*C07K 1/00* (2006.01)

(52) U.S. Cl. .................. 435/69.1; 435/183; 530/402

(58) Field of Classification Search .................. None
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 5,235,041 | A | 8/1993 | Cappello et al. |
| 5,766,897 | A * | 6/1998 | Braxton ............ 435/463 |
| 5,792,742 | A | 8/1998 | Gold et al. |
| 5,932,462 | A | 8/1999 | Harris et al. |
| 6,207,446 | B1 | 3/2001 | Szostak et al. |
| 6,462,189 | B1 | 10/2002 | Koide |
| 6,610,281 | B2 | 8/2003 | Harris |
| 6,818,418 | B1 | 11/2004 | Lipovsek et al. |
| 7,115,396 | B2 * | 10/2006 | Lipovsek et al. ..... 435/69.1 |
| 7,847,062 | B2 | 12/2010 | Chen et al. |
| 7,858,739 | B2 | 12/2010 | Chen et al. |
| 2002/0019517 | A1 | 2/2002 | Koide |
| 2002/0061307 | A1 | 5/2002 | Whitlow et al. |
| 2003/0134352 | A1 | 7/2003 | Freimuth et al. |
| 2003/0170753 | A1 | 9/2003 | Koide |
| 2004/0142429 | A1 | 7/2004 | Grant et al. |
| 2004/0146969 | A1 | 7/2004 | Furutani et al. |
| 2005/0255548 | A1 | 11/2005 | Lipovsek et al. |
| 2007/0031955 | A1 | 2/2007 | Lee et al. |
| 2008/0125580 | A1 | 5/2008 | Pizarro et al. |
| 2009/0054628 | A1 | 2/2009 | St. John et al. |

FOREIGN PATENT DOCUMENTS

| | | |
|---|---|---|
| JP | 04-108827 A | 4/1992 |
| WO | WO-98/31700 A1 | 7/1998 |
| WO | WO-98/56915 A2 | 12/1998 |
| WO | WO-00/34784 | 6/2000 |
| WO | WO-01/64942 | 9/2001 |
| WO | WO-02/04523 A2 | 1/2002 |
| WO | WO-02/32925 | 4/2002 |
| WO | WO-2004/113394 A2 | 12/2004 |
| WO | WO-2008/097497 | 8/2008 |
| WO | WO-2009/025806 | 2/2009 |
| WO | WO-2009/073115 | 6/2009 |
| WO | WO-2009/142773 A2 | 11/2009 |
| WO | WO-2010/060095 A1 | 5/2010 |

OTHER PUBLICATIONS

Kim et al. In vitro refolding of PEGylated lipase. J. Biotechnol. 131 (2007) 177-179.*

Abuchowski et al., Alteration of Immunological Properties of Bovine Serum Albumin by Covalent Attachement of Polyethylene Glycol, *J. Biol. Chem.*, 252:3578-3581 (1977).

Abuchowski et al., Effect of Covalent Attachment of Polyethylene Glycol on Immunogenicity and Circulating Life of Bovine Liver Catalase, *J. Biol. Chem.*, 252:3582-3586 (1977).

Baron et al. H NMR Assignment and Secondary Structure of the Cell Adhesion Type III Module of Fibronectin. *Biochemistry*, 31:2068-2073 (1992).

Batori et al., Exploring the Potential of the Monobody Scaffold: Effects of Loop Elongation on the Stability of a Fibronectin Type III Domain, *Protein Eng.*, 15(12):1015-1020 (2002).

Caliceti, P., et al., "Pharmacokinetic and biodistribution properties of poly(ethylene glycol)—protein conjugates," *Advanced Drug Delivery Reviews*, 55:1261-1277 (2003).

Campbell & Spitzfaden, Building Proteins with Fibronectin Type III Modules, *Structure*, 2(5):333-337 (1994).

J Choy et al., Efficacy of a Novel PEGylated Humanized Anti-TNF Fragment (CDP870) in Patients with Rheumatoid Arthritis: a Phase II Double-Blinded, Randomized, Dose-Escalating Trial. *Rheumatology*, 41:1133-1137 (2002).

Clarke et al., Folding and Stability of a Fibronectin Type III Domain of Human Tenascin. *J. Mol. Biol.*, 270: 771-778 (1997).

Cleland et al., Polyethylene Glycol Enhanced Refolding of Bovine Carbonic Anhydrase B, *The Journal of Biological Chemistry*, 267(19):13327-13334 (1992).

Copie et al., Solution Structure and Dynamics of Linked Cell Attachment Modules of Mouse Fibronectin Containing the RGD and Synergy Regions: Comparison with the Human Fibronectin Crystal Structure. *J. Mol. Biol.* 277:663-682 (1998).

Dickinson et al., Crystal Structure of the Tenth Type III Cell Adhesion Module of Human Fibronectin. *J. Mol. Biol.* 236:1079-1092 (1994).

Dickinson et al., Crystals of the Cell-Binding Module of Fibronectin Obtained from a Series of Recombinant Fragments Differing in Length. *J. Mol. Biol.* 238:123-127 (1994).

Grant et al., Structural Requirements for Biological Activity of the Ninth and Tenth Fill Domains of Human Fibronectin. *J. Biol. Chem.* 272:6159-6166 (1997).

(Continued)

Primary Examiner — Nashaat Nashed
(74) *Attorney, Agent, or Firm* — Ropes & Gray LLP

(57) ABSTRACT

Provided herein are methods for refolding proteins. The methods involve covalently modifying a denatured protein with a nonproteinaceous polymer and then renaturing the modified protein.

27 Claims, No Drawings

OTHER PUBLICATIONS

Hocking et al., A Novel Role for the Integrin-Binding III-10 Module in Fibronectin Matrix Assembly. *J. Cell Biol.* 133:431-444 (1996).

Koide et al., Stabilization of a Fibronectin Type III Domain by the Removal of Unfavorable Electrostatic Interactions on the Protein Surface, *Biochemistry*, 40(34):10326-10333 (2001).

Koide et al., The Fibronectin Type III Domain as a Scaffold for Novel Binding Proteins. *J. Mol. Biol.* 284:1141-1151 (1998).

Leahy et al., Structure of a Fibronectin Type III Domain from Tenascin Phased by MAD Analysis of the Selenomethionyl Protein. *Science* 258:987-991 (1992).

Leahy et al., "2.0 A Crystal Structure of Four-Domain Segment of Human Fibronectin Encompassing the RGD Loop and Synergy Region," *Cell*, 84:155-164 (1996).

Litvinovich and Ingham, Interactions Between Type III Domains in the 110 kDa Cell-Binding Fragment of Fibronectin. *J. Mol. Biol.* 248:611-626 (1995).

Lombardo et al., Conformational Flexibility and Crystallization of Tandemly Linked Type III Modules of Human Firbonectin. *Prot. Sci.* 5:1934-1938 (1996).

Main et al., The Three-Dimensional Structure of the Tenth Type III Module of Fibronectin: An Insight into RGD-Mediated Interactions. *Cell* 71:671-678 (1992).

Matsushima et al. Modification of *E. coli* Asparaginase with 2,4-BIS(O-Methoxypolyethylene Glycol)-6-Chloro-S-Triazine (Activated PEG2); Disappearance of Binding Ability Towards Anti-Serum and Retenttion of Enzymic Activity. *Chemistry Letters*, p. 773-776 (1990).

Parker et al., "Antibody mimics based on human fibronectin type three domain engineered for thermostability and high-affinity binding to vascular endothelial growth factor receptor two", *Protein Engineering, Design & Selection*, 18(9):435-444 (2005).

Plaxco et al. A Comparison of the Folding Kinetics and Thermodynamics of Two Homologous Fibronectin Type III Modules. *J. Mol. Biol.* 270:763-770 (1997).

Plaxco et al. Rapid Refolding of a Proline-Rich All-Beta-Sheet Fibronectin Type III Module. *PNAS* 93:10703-10706 (1996).

Potts and Campbell. Structure and Function of Fibronectin Modules. *Matrix Biol.* 15:313-320 (1996).

Richards, J., et al., "Engineered Fibronectin Type III Domain with a RGDWXE Sequence Binds with Enhanced Affinity and Specificity to Human $\alpha v\beta 3$ Integrin," *J. Mol. Biol. Science Direct.* 326:1475-1488 (2003).

Roberts and Szostak. RNA-Peptide Fusions for the In Vitro Selection of Peptides and Proteins. *PNAS* 94:12297-12302 (1997).

Roberts et al., Chemistry for peptide and protein PEGylation, *Advanced Drug Delivery Reviews*, 54:459-476 (2002).

Roberts, R.W. Totally in vitro protein selection using mRNA-protein fusions and ribosome display. Current Opinion in Chemical Biology, Current Biology Ltd, London, GB, 3, 268-273 (1999), XP002180767 ISSN: 1367-5931.

Ryan et al., Advances in PEGylation of imprtant biotech molecules: delivery aspects, *Expert Opin. Drug Deliv.* 5(4):371-383 (2008).

Xu et al., Directed Evolution of High-Affinity Antibody Mimics Using mRNA Display, *Chemistry & Biology*, 9:933-942 (2002).

Yang et al., "Tailoring Structure-Function and Pharmacokinetic Properties of Single-Chain Fv Proteins by Site-Specific PEGylation", *Protein Engineering*, 16(10):761-770 (2003).

\* cited by examiner

METHODS FOR PROTEIN REFOLDING

RELATED APPLICATIONS

This application claims the benefit of U.S. Provisional Application Ser. No. 61/212,990, filed Apr. 17, 2009. All of the teachings of the above-referenced provisional application are incorporated herein by reference.

SEQUENCE LISTING

The instant application contains a Sequence Listing which has been submitted via EFS-Web and is hereby incorporated by reference in its entirety. Said ASCII copy, created on Jun. 4, 2010, is named COTH5281.txt and is 4,413 bytes in size.

BACKGROUND

Many recombinant proteins are produced in a variety of host organisms. Most proteins can be expressed in their native form in eukaryotic hosts such as CHO cells. Animal cell culture generally requires prolonged growing times to achieve maximum cell density and often require expensive media containing growth components that may interfere with the recovery of the desired protein. Bacterial host expression systems provide a cost-effective alternative to the manufacturing scale production of recombinant proteins. Recombinant proteins overexpressed in *Escherichia coli* are often accumulated as insoluble particles called inclusion bodies. Since proteins in inclusion bodies are usually inactive, they must be solubilized by a denaturing agent and refolded to recover their active form. When producing proteins, it is generally desirable to obtain a high refolding efficiency and high throughput at high protein concentrations.

There is a need for new and more effective methods of folding and/or recovering recombinant proteins from a host cell culture, e.g., for the efficient and economical production of recombinant proteins in bacterial cell culture.

SUMMARY

In one aspect, the application provides a method for refolding a protein comprising covalently modifying a denatured protein with a nonproteinaceous polymer and renaturing the covalently modified protein. In certain embodiments, the nonproteinaceous polymer is a polyethylene glycol (PEG). Suitable PEGs include PEGs having a molecular weight of from 5-200 kDa, from 5-150 kDa, from 5-100 kDa, 5-50 kDa, 20-80 kDa, 20-60 kDa, 20-40 kDa, or 40-60 kDa. The PEG may be linear, branched or comb-type. In certain embodiments, the nonproteinaceous polymer is attached to the protein through a cleavable linker. In certain embodiments, the protein is covalently modified with the nonproteinaceous polymer at a site specific location, for example, a PEG molecule may be covalently attached to a protein through a lysine or cysteine residue. Alternatively, a PEG molecule may be covalently attached to a protein through the N-terminus or C-terminus of the protein.

In certain embodiments, the methods described herein may further comprise removing the nonproteinaceous polymer after renaturing the covalently modified protein.

In certain embodiments, the denatured protein was expressed in bacterial cells, such as, for example, *E. coli*. In certain embodiments, the denatured protein was isolated from inclusion bodies.

In certain embodiments, the denatured protein was subjected to denaturing conditions such as, for example, mechanical denaturation, denaturation by exposure to high or low temperature, suboptimal pH, detergents, high salt concentration, or chaotropic agents, or by chemically cleaving disulfide bonds.

In certain embodiments, the protein is denatured using a chaotropic agent, such as, for example, guanidine hydrochloride, urea, sodium hydroxide or potassium hydroxide, and renatured by removing the chaotropic agent, for example, by dialysis.

In certain embodiments, the protein being refolded comprises an Fn3 domain.

In another aspect, the application provides a method for producing a pegylated protein, comprising: (a) expressing a recombinant protein in bacterial cells, (b) isolating the recombinant protein from inclusion bodies, (c) covalently modifying the recombinant protein with PEG, and (d) renaturing the pegylated recombinant protein.

In another aspect, the application provides a method for producing a pegylated protein, comprising: (a) expressing a recombinant protein in bacterial cells, (b) isolating the recombinant protein from inclusion bodies, (c) exposing the recombinant protein to a chaotropic agent, (d) covalently modifying the recombinant protein with PEG, (e) renaturing the pegylated recombinant protein by removing the chaotropic agent, and (f) purifying the refolding, pegylated, recombinant protein.

In another aspect, the application provides a method for producing a protein, comprising: (a) expressing a recombinant protein in bacterial cells, (b) isolating the recombinant protein from inclusion bodies, (c) covalently modifying the recombinant protein with PEG, (d) renaturing the pegylated recombinant protein, and (e) removing the PEG from the recombinant protein.

Any desired protein may be produced using the methods described herein. In exemplary embodiments, the protein produced by the methods of the invention is a protein that is insoluble or only partially soluble in an aqueous solution or as produced in a host cell. Examples of proteins that may be produced by the methods described herein include, for example, polypeptides comprising an Fn3 domain, antibodies and antibody fragments.

DETAILED DESCRIPTION

Overview

Many proteins behave poorly in their solubly expressed and purified state. These materials often express as inclusion bodies inside *E coli* cells or mixtures of inclusion bodies and cytosolic soluble proteins. Still other expressed proteins can be found in the cytosol almost exclusively but prove difficult to handle during purification because of a propensity to self aggregate and precipitate out of solution. Such molecules stick readily to one another and fall out of solution. For inclusion body produced proteins, the protein material is denatured with chaotropic reagents such as guanidine hydrochloride (Gdn-HCl) or Urea. The solubilized, denatured protein is then depleted in chaotrope using one of a variety of methods yielding a soluble, natively folded protein.

We have surprisingly found that we can Pegylate many of these proteins while in the denatured state and then successfully refold these proteins to their active folded state. This method enables one to create pegylated proteins at useful concentrations that otherwise may not be attainable due to the difficulty in keeping the proteins of interest in solution long enough to pegylate them. There is no need to purify the protein to its soluble, folded state prior to PEGylation. In fact, there are often significant advantages to PEGylating the protein while in the denatured state. For example, the method saves time as the combined step circumvents the need to fold the protein of interest first and then PEGylate. This method may be particularly suited for folded proteins of limited solubility in buffers and pH amenable to the PEGylation reaction. While not wishing to be bound by theory, the covalently linked PEG may be acting as a "chaperone" preventing aggregation of the protein in the denatured and renatured states. In addition, we found that this method allowed us to vastly increase our ability to refold certain proteins that could not readily be refolded using more standard procedures.

The methods described herein involve covalently attaching a nonproteinaceous polymer, such as a PEG, to a denatured protein and then refolding the protein. The proteins to be refolded may be denatured by any means known in the art, such as, for example, mechanical denaturation, denaturation by exposure to high or low temperature, suboptimal pH, detergents, high salt concentration, or chaotropic agents, or by chemically cleaving disulfide bonds. Refolding or renaturation of the covalently modified protein may be carried out using standard procedures known in the art for refolding proteins. For example, thermally denatured proteins may be refolded by lowering the temperature of the protein solution. Chemically denatured proteins may be refolded by removing the denaturant from the protein solution or diluting the solution. In an exemplary embodiment, the denaturing agent is a chaotropic agent, such as, for example, guanidine hydrochloride, urea, sodium hydroxide or potassium hydroxide, and renatured by removing the chaotropic agent, for example, by dialysis.

The methods described herein may be used to produce proteins that are insoluble or partially insoluble. When proteins are only partially insoluble, it may be desirable to increase the proportion of insoluble protein during expression. For example, when expressing proteins in $E.\ coli$, the cell culture may be grown at a higher temperature (e.g., 37° C. or 42° C.) in order to increase the proportion of the recombinant protein in inclusion bodies. The protein is then isolated from the inclusion bodies and subjected to the refolding methods described herein.

In certain embodiments, a protein to be refolded may be covalently modified with a single nonproteinaceous polymer molecule, or with two, three, four or more nonproteinaceous polymer molecules. The nonproteinaceous polymers may be attached to the protein to be refolded in a site specific manner (as described below) or in a non-site specific manner.

In certain embodiments, it is desirable to produce a pegylated protein as the final product. In this case, a PEG molecule is covalently attached to the denatured protein and then refolded and the PEG is maintained on the refolded molecule. In other embodiments, the PEG, or other nonproteinaceous polymer, is not desired on the final product. In this situation, the denatured protein is covalently modified with the nonproteinaceous polymer, the protein is refolded and then the nonproteinaceous polymer may be removed from the folded protein. In such embodiments, the polymer may be removed from the protein using any of a variety of methods. For example, the polymer may be chemically or enzymatically cleaved from the protein. In certain embodiments, the polymer may be attached to the protein through a cleavable linker. In certain embodiments, the polymer may be removed by cleaving the refolded protein with a protease that removes a portion of the amino acid sequence containing the covalently attached polymer. In such embodiments, the protein to be refolded may be expressed as a fusion protein containing a peptide tag fused to the protein of interest. The peptide tag may be used as the site for covalent attachment of the polymer. The peptide tag can contain a protease cleavage site such that it can be removed from the protein of interest along with the covalently attached polymer. In exemplary embodiments, a peptide tag may be fused to a protein of interest at the C-terminus, N-terminus or at both the C-terminus and N-terminus of the protein.

In certain embodiments, the methods described herein may be used to produce proteins that are difficult to refold. For example, a protein that is hard to productively refold may be amenable to refolding after it has been covalently modified with a nonproteinaceous polymer, such as a PEG. Afterwards, if desired, the PEG (or other polymer) can be removed by a variety of cleavage mechanisms as described herein. Since the folded state of a protein is more stable/soluble than its unfolded self, difficult to refold proteins may be produced using the methods described herein. After the protein has been refolded and is therefore more stable and/or soluble, the PEG (or other polymer) can then be removed if desired.

In certain embodiments, the methods described herein may be used to refold proteins that cannot be refolded by other conventional refolding methods. In other embodiments, the methods described herein may be used to enhance or increase the level of protein that is refolded as compared to other conventional refolding methods. For example, the level of protein refolding may be increased by at least 10%, 20%, 50%, 75%, 80%, or 90% relative to the level of refolding achieved for the same protein using a different method, or the level of protein refolding may be increased by at least 2-fold, 3-fold, 4-fold, 5-fold, or 10-fold relative to the level of refolding achieved for the same protein using a different method.

PEGylation

The methods described herein involve covalently linking a nonproteinaceous polymer to a protein to be refolded. In some embodiments, the polymer is polyethylene glycol ("PEG"), polypropylene glycol, or polyoxyalkylenes, as described in U.S. Pat. No. 4,640,835; 4,496,689; 4,301,144; 4,670,417; 4,791,192 or 4,179,337. In some embodiments, the polymer is a PEG moiety.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O (CH$_2$CH$_2$O)$_{n-1}$CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, European Published Application No. 473084A and U.S. Pat. No. 5,932,462. One form of PEGs includes two PEG side-chains (PEG2) linked via the primary amino groups of a lysine (Monfardini, C., et al., Bioconjugate Chem. 6 (1995) 62-69).

PEG conjugation to peptides or proteins generally involves the activation of PEG and coupling of the activated PEG-intermediates directly to target proteins/peptides or to a linker, which is subsequently activated and coupled to target proteins/peptides (see Abuchowski, A. et al, *J. Biol. Chem.*, 252, 3571 (1977) and *J. Biol. Chem.*, 252, 3582 (1977), Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

There are many different types of PEG, ranging from molecular weights of below 300 g/mol to over 10,000,000 g/mol. PEG chains can be linear, branched, or with comb (i.e., a polymer comprising one or more main chains with multiple trifunctional branch points from each of which a linear side-chain emanates) or star geometries. In particular embodiments, PEG may be attached to the protein as a comb polymer (see for example WO2004/113394).

The size of PEG utilized may vary and in certain embodiments may depend on several factors including the intended use of the pegylated protein. For example, larger PEGs are preferred to increase half life of a protein in the body, blood, non-blood extracellular fluids or tissues. For in vivo cellular activity, PEGs of the range of about 10 to 60 kDa are preferred, as well as PEGs less than about 100 kDa and more preferably less than about 60 kDa, though sizes greater than about 100 kDa can be used as well. For in vivo imaging application, smaller PEGs, generally less than about 20 kDa, may be used that do not increase half life as much as larger PEGs so as to permit quicker distribution and less half life. A variety of molecular mass forms of PEG can be selected, e.g., from about 1,000 Daltons (Da) to 100,000 Da (n is 20 to 2300), for conjugating to binding polypeptides of the invention. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270). In some embodiments, one PEG moiety is conjugated to a desired protein. In some embodiments, the PEG moiety is about 20, 30, 40, 50, 60, 70, 80, or 90 KDa. In some embodiments, the PEG moiety is about 40 KDa.

In some embodiments, PEGylated proteins may contain one, two or more PEG moieties. In one embodiment, the PEG moiety(ies) are bound to an amino acid residue which is on the surface of the protein when folded and/or away from the surface that contacts a target ligand. In one embodiment, the combined or total molecular mass of PEG in PEG-binding polypeptide is from about 3,000 Da to 60,000 Da, or from about 10,000 Da to 36,000 Da. In a one embodiment, the PEG in pegylated binding polypeptide is a substantially linear, straight-chain PEG.

One skilled in the art can select a suitable molecular mass for PEG, e.g., based on how the pegylated binding polypeptide will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 10: 91-114 (1993).

In some embodiments, a desired polypeptide is covalently linked to one poly(ethylene glycol) group of the formula: —CO—$(CH_2)_x$—$(OCH_2CH_2)_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's ε-amino group of a lysine is the available (free) amino group.

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (see U.S. Pat. No. 5,281,698 and U.S. Pat. No. 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively.

Pegylation of a desired polypeptide can be performed according to the methods of the state of the art. In certain embodiments, PEG may be bound to the protein through a chemical linker. The linker may be attached to the PEG and protein by any suitable bond or functional group, including carbon-carbon bonds, esters, ethers, amides, amines, carbonates, carbamates, sulfonamides, etc. Exemplary linkers are well known in the art and include, for example, disulfide groups, ether groups, thioether groups, amino groups, carbonyl comprising groups, e.g., amides, esters, ketones, acid labile groups, photolabile groups, peptidase labile groups and esterase labile groups. In exemplary embodiments, the linker may be selected from any of —C(=O)—, —C(=S)—, —C(=NR$^1$)—, —S(=O)—, —S(=O)$_2$—, —C(=O)O—, —C(=O)NH—, —NR$^1$—, —O—, —S—, —S—S—, —(CR$^1$R$^2$)—, —NR$^1$—NR$^1$—, —NR$^1$—C(O)—, $C_1$-$C_4$ alkylene, —S—($C_1$-$C_4$) alkylene and —NR$^1$—($C_1$-$C_4$) alkylene-wherein R$^1$ and R$^2$ are independently selected from hydrogen and optionally substituted $C_1$-$C_4$ alkyl.

In certain embodiments, the chemical linker is stable under physiological conditions, e.g., an alkylene chain. In certain embodiments, the linker is cleavable under physiological conditions, such as by an enzyme (e.g., the linkage contains a peptide sequence that is a substrate for a peptidase), or by hydrolysis (e.g., the linkage contains a hydrolyzable group, such as an ester or thioester). In certain embodiments, the linker is cleaved when exposed to any one or combination of conditions known in the art for cleaving chemical linkages such as enzymes, heat, light or chemical reagents. In certain embodiments, the linker may be cleaved once the PEGylated protein has been renatured. In particular embodiments, the linker is unreactive under the conditions which denature the protein.

In certain embodiments, PEG may be bound to the protein directly through a chemical bond. For example, PEG may be covalently linked to the protein by reaction of the polypeptide with electrophilically active PEGs (supplier: Shearwater Corp., USA, world wide web at shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C., et al., Bioconjugate Chem. 6 (1995) 62-69). Such methods may used to pegylated at a ε-amino group of a binding polypeptide lysine or the N-terminal amino group of the binding polypeptide.

In another embodiment, PEG molecules may be coupled to sulfhydryl groups on a binding polypeptide (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments, the pegylated polypeptide is produced by site-directed pegylation, particularly by conjugation of PEG to a cysteine moiety at the N- or C-terminus A PEG moiety may also be attached by other chemistry, including by conjugation to amines.

In some embodiments where PEG molecules are conjugated to cysteine residues on a binding polypeptide, the cysteine residues are native to the binding polypeptide, whereas in other embodiments, one or more cysteine residues are engineered into the binding polypeptide. Mutations may be introduced into a binding polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework based on which binding polypeptides are designed and evolved has been solved (see Himanen et al., Nature. (2001) 20-27; 414(6866):933-8) and thus the surface-exposed residues identified. In one embodiment, cysteine residues are introduced into binding polypeptides at or near the N- and/or C-terminus, or within loop regions. Pegylation of cysteine residues may be carried out using, for example, PEG-maleiminde, PEG-vinylsulfone, PEG-iodoacetamide, or PEG-orthopyridyl disulfide.

In some embodiments, the pegylated binding polypeptide comprises a PEG molecule covalently attached to the alpha amino group of the N-terminal amino acid. Site specific N-terminal reductive amination is described in Pepinsky et al., (2001) JPET, 297, 1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254, 12579, and in Chamow et al., (1994) Bioconjugate Chem. 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Publication No. 2002/0044921 and PCT Publication No. WO94/01451.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, *Bioconjug Chem.* 2004; 15(5):1005-1009.

Conventional separation and purification techniques known in the art can be used to purify PEGylated binding polypeptide, such as size exclusion (e.g., gel filtration) and ion exchange chromatography. Products may also be separated using SDS-PAGE. Products that may be separated include mono-, di-, tri- poly- and un-pegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

Vectors & Polynucleotides Embodiments

Nucleic acids encoding a desired protein or polypeptide may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 Jan. 21; 100(2):438-42; Sinclair et al. Protein Expr Purif. 2002 October; 26(1):96-105; Connell N D. Curr Opin Biotechnol. 2001 October; 12(5):446-9; Makrides et al. Microbiol. Rev. 1996 September; 60(3):512-38; and Sharp et al. Yeast. 1991 October; 7(7):657-78.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The proteins of interest may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO90/13646. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

Expression and cloning vectors usually contain a promoter that is recognized by the host organism and is operably linked to the nucleic acid encoding the protein of the invention, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the protein of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP Patent Publication No. 73,657. Yeast enhancers also are advantageously used with yeast promoters.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al., Nature 297:598-601 (1982) on expression of human.beta.-interferon cDNA in mouse cells under the control of a thymidine kinase promoter from herpes simplex virus. Alternatively, the rous sarcoma virus long terminal repeat can be used as the promoter.

Transcription of a DNA encoding proteins of the invention by higher eukaryotes is often increased by inserting an enhancer sequence into the vector. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the protein encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide. One useful transcription termination component is the bovine growth hormone polyadenylation region. See WO94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, E. coli or Bacillus spp. Yeast, preferably from the Saccharomyces species, such as S. cerevisiae, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, expression in E. coli is the preferred method for expression. The protein is then purified from culture media or cell extracts.

Other suitable eukaryotic host cells for the expression proteins are derived from multicellular organisms. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection are publicly available, e.g., the L-1 variant of Autographa californica NPV and the Bm-5 strain of Bombyx mori NPV, and such viruses may be used as the virus herein according to the present invention, particularly for transfection of Spodoptera frugiperda cells.

In some instance it will be desired to produce proteins in vertebrate cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59. (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; a human hepatoma line (Hep G2); and myeloma or lymphoma cells (e.g., Y0, J558L, P3 and NS0 cells) (see U.S. Pat. No. 5,807,715). Plant cell cultures of cotton, corn, potato, soybean, petunia, tomato, and tobacco can also be utilized as hosts.

Protein Production

Host cells are transformed with a suitable expression or cloning vector as described herein for protein production and cultured in conventional nutrient media modified as appropriate for inducing promoters, selecting transformants, or amplifying the genes encoding the desired sequences.

The host cells used to produce a desired protein according the methods described herein may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), (Sigma)) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927, 762; 4,560,655; or 5,122,469; WO90/03430; WO87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

Proteins can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The proteins can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Fibronectins

In an exemplary embodiment, the methods disclosed herein may be used to produce polypeptides comprising at least one Fn3 domain or multivalent polypeptides comprising two or more Fn3 domains covalently linked via a polypeptide linker In certain embodiments, the methods disclosed herein may be used to produce polypeptides comprising at least one tenth domain of fibronectin ($^{10}$Fn3 domain) or multivalent polypeptides comprising two or more $^{10}$Fn3 domains.

Fibronectin based scaffolds are a family of proteins capable of evolving to bind any compound of interest. These proteins, which generally make use of a scaffold derived from a fibronectin type III (Fn3) or Fn3-like domain, function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions that normally lead to the loss of structure and function in antibodies. An example of fibronectin-based scaffold proteins are Adnectins™ (Adnexus, a Bristol-Myers Squibb R&D Company).

Fibronectin is a large protein which plays essential roles in the formation of extracellular matrix and cell-cell interactions; it consists of many repeats of three types (types I, II, and III) of small domains (Baron et al., 1991). Fn3 itself is the paradigm of a large subfamily which includes portions of cell adhesion molecules, cell surface hormone and cytokine receptors, chaperoning, and carbohydrate-binding domains. For reviews see Bork & Doolittle, Proc Natl Acad Sci USA. 1992 Oct. 1; 89(19):8990-4; Bork et al., J Mol. Biol. 1994 Sep. 30; 242(4):309-20; Campbell & Spitzfaden, Structure. 1994 May 15; 2(5):333-7; Harpez & Chothia, J Mol. Biol. 1994 May 13; 238(4):528-39).

Fibronectin type III (Fn3) domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. Any or all of loops AB, BC, CD, DE, EF and FG may participate in target binding. The BC, DE, and FG loops are both structurally and functionally analogous to the complementarity determining regions (CDRs) from immunoglobulins U.S. Pat. No. 7,115,396 describes Fn3 domain proteins wherein alterations to the BC, DE, and FG loops result in high affinity TNFα binders. U.S. Publication No. 2007/0148126 describes Fn3 domain proteins wherein alterations to the BC, DE, and FG loops result in high affinity VEGFR2 binders.

EXEMPLIFICATION

The invention now being generally described, it will be more readily understood by reference to the following examples which are included merely for purposes of illustration of certain aspects and embodiments of the present invention, and are not intended to limit the invention in any way.

Example 1

Pegylation of Multivalent $^{10}$Fn3 Binders

Two multivalent $^{10}$Fn3 binders having two monomeric $^{10}$Fn3 domains attached via a polypeptide linker were produced using the following method. The multivalent $^{10}$Fn3 polypeptides comprised one subunit that bound to EGFR and one subunit that bound to IGF-IR and were referred to as E/I binders. The E/I $^{10}$Fn3-based binders were E2-GS10-I1-cys (with his) (SEQ ID NO: 1) and E3-GS10-I1-Cys (with his) (SEQ ID NO: 2). Five ml of an inoculum culture of BL21 (DE3) E. coli cells containing a T7 ploymerase driven pET29 plasmid encoding either E2-GS10-I1-cys (with his) or E3-GS10-I1-Cys (with his), were generated from a single plated colony and used to inoculate 1 liter of auto-induction media (EMD Biosciences, San Diego, Calif.) containing 50 μg/mL kanamycin. Expression was carried out at 18° C. after initial growth at 37° C. and harvested by centrifugation for 10 minutes at ~10,000×g at 4° C. Cell pellets were frozen at 80° C. The cell pellet was resuspended in 10 mL of lysis buffer (20 mM NaH$_2$PO$_4$, 0.5 M NaCl, 5 mM Immidazole, pH 7.4) and mechanically lysed using an Avestin homgenizer. The soluble fraction was separated by centrifugation for 15 minutes at 23,300×g at 4° C. The supernatant was decanted and the pellet was solubilized in Lysis buffer (above) supplemented with 4 M to 6 M guanidine hydrochloride (GdnHCl). Solubilized protein was then purified on a suitably sized NiNTA column (Qiagen, Inc.) pre-equilibrated with the GdnHCL supplemented Lysis Buffer. The column was then washed with 5 to 10 column volumes of the same buffer, followed by elution with the same buffer supplemented with 300 mM Immidazole. The fractions eluted off the column containing the protein of interest were diluted to 2-3 mgs/mL protein and then combined with a 1.2-1.5 molar excess of solid NEM-PEG (40 kDa branched or other). The mixture was allowed to react at room temperature for 30 minutes or until the reaction was complete. The entire reaction volume was then placed into a dialysis bag (5,000 Da Molecular Weight cutoff) and the mixture was subjected to a dialysis refolding process. For example, this process may consist of two 10-16 hour 500:1 (buffer:dialysate) dialysis exchanges against 50 mM NaOAc, 150 mm NaCl, pH 4.5. The dialysate from this procedure contains properly folded, PEGylated materials plus excess reactants. The mixture of products and excess reactants from the PEGylation reaction were clarified via centrifugation or filtration prior to loading them onto a cation exchange chromotography column (SP Sepharose or Resource S, GE Healthcare). The column was developed with 150 mM to 1 M NaCl gradient in the NaOAc background buffer. Confirmation of the PEGylation of the protein can be confirmed by SDS-Page and/or SE-HPLC methods that can separate the non-PEGylated protein from the PEGylated protein.

Amino Acid Sequence of E2-GS10-I1-cys
(with his)
(SEQ ID NO: 1)
MGVSDVPRDLEVVAATPTSLLISWDSGRGSYQYYRITYGETGGNSPV

QEFTVPGPVHTATISGLKPGVDYTITVYAVTDHKPHADGPHTYHES

PISINYRTEIDKGSGSGSGSGSGSGSGSGSGSVSDVPRDLEVVAAT

PTSLLISWSARLKVARYYRITYGETGGNSPVQEFTVPKNVYTATI

SGLKPGVDYTITVYAVTRFRDYQPISINYRTEIDKPCQHHHHHH

Amino Acid Sequence of E3-GS10-I1-Cys
(with his)
(SEQ ID NO: 2)
MGVSDVPRDLEVVAATPTSLLISWLPGKLRYQYYRITYGETGGNS

PVQEFTVPHDLRTATISGLKPGVDYTITVYAVTNMMHVEYSEYPI

SINYRTEIDKGSGSGSGSGSGSGSGSGSGSVSDVPRDLEVVAATP

TSLLISWSARLKVARYYRITYGETGGNSPVQEFTVPKNVYTATIS

GLKPGVDYTITVYAVTRFRDYQPISINYRTEIDKPCQHHHHHH

Incorporation By Reference

All documents and references, including patent documents and websites, described herein are individually incorporated by reference to into this document to the same extent as if there were written in this document in full or in part. In case of conflict, the present application, including any definitions herein, will control.

What is claimed is:

1. A method for refolding a protein comprising covalently modifying a denatured protein with a nonproteinaceous polymer and renaturing the covalently modified protein, wherein the method comprises removing the nonproteinaceous polymer after renaturing the covalently modified protein.

2. The method of claim 1, wherein the nonproteinaceous polymer is polyethylene glycol (PEG) polymer.

3. The method of claim 2, wherein the PEG has a molecular weight of 20 kDa to 80 kDa.

4. The method of claim 2, wherein the PEG is linear.

5. The method of claim 2, wherein the PEG is branched.

6. The method of claim 1, wherein the nonproteinaceous polymer is attached to the protein through a cleavable linker.

7. The method of claim 1, wherein the protein is covalently modified with the nonproteinaceous polymer at a site specific location.

8. The method of claim 2, wherein the PEG is covalently attached to the protein at a cysteine residue.

9. The method of claim 1, wherein the denatured protein was expressed in bacterial cells.

10. The method of claim 9, wherein the bacterial cells are *E. coli*.

11. The method of claim 9, wherein the denatured protein was isolated from inclusion bodies.

12. The method of claim 1, wherein the protein was denatured by addition of detergents, or chaotropic agents.

13. The method of claim 12, wherein the disulfide bonds of the protein were chemically cleaved.

14. The method of claim 12, wherein the protein was denatured using a chaotropic agent.

15. The method of claim 14, wherein the protein is renatured by removing the chaotropic agent.

16. The method of claim 15, wherein the chaotropic agent is removed using dialysis.

17. The method of claim 1, wherein the protein comprises a tenth fibronectin Type III ($^{10}$Fn3) domain.

18. The method of claim 17, wherein the protein comprises two $^{10}$Fn3 domains.

19. A method for producing a protein, comprising:
a) expressing a recombinant protein in bacterial cells,
b) isolating the recombinant protein from inclusion bodies,
c) covalently modifying the recombinant protein with PEG,
d) renaturing the pegylated recombinant protein, and
e) removing the PEG from the recombinant protein.

20. The method of claim 19, wherein the recombinant protein comprises a tenth fibronectin Type III ($^{10}$Fn3) domain.

21. A method for refolding a protein comprising covalently modifying a denatured protein with a nonproteinaceous polymer and renaturing the covalently modified protein, wherein the nonproteinaceous polymer is attached to the protein through a protease cleavable linker.

22. The method of claim 21, wherein the nonproteinaceous polymer is polyethylene glycol (PEG) polymer.

23. The method of claim 21, wherein the protein comprises a tenth fibronectin Type III ($^{10}$Fn3) domain.

24. A method for producing a pegylated protein, comprising:
a) expressing a recombinant protein in bacterial cells,
b) isolating the recombinant protein from inclusion bodies,
c) covalently modifying the recombinant protein with PEG, and
d) renaturing the pegylated recombinant protein,
wherein the PEG is attached to the recombinant protein through a protease cleavable linker.

25. The method of claim 24, wherein the recombinant protein comprises a tenth fibronectin Type III ($^{10}$Fn3) domain.

26. A method for producing a pegylated protein, comprising:
a) expressing a recombinant protein in bacterial cells,
b) isolating the recombinant protein from inclusion bodies,
c) exposing the recombinant protein to a chaotropic agent,
d) covalently modifying the recombinant protein with PEG, e) renaturing the pegylated recombinant protein by removing the chaotropic agent,
f) purifying the refolded, pegylated, recombinant protein, and
g) removing the PEG from the recombinant protein.

27. The method of claim 26, wherein the recombinant protein comprises a tenth fibronectin Type III ($^{10}$Fn3) domain.

* * * * *

SEQUENCE LISTING

<160> NUMBER OF SEQ ID NOS: 2

<210> SEQ ID NO 1
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
                20                  25                  30

Tyr Tyr Arg Ile Thr Tyr Gly Glu Thr Gly Gly Asn Ser Pro Val Gln
            35                  40                  45

Glu Phe Thr Val Pro Gly Pro Val His Thr Ala Thr Ile Ser Gly Leu
    50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Gly Ser Gly Ser Gly Ser Gly
            100                 105                 110

Ser Gly Ser Gly Ser Gly Ser Gly Ser Gly Ser Val Ser Asp
        115                 120                 125

Val Pro Arg Asp Leu Glu Val Val Ala Ala Thr Pro Thr Ser Leu Leu
130                 135                 140

Ile Ser Trp Ser Ala Arg Leu Lys Val Ala Arg Tyr Tyr Arg Ile Thr
145                 150                 155                 160

Tyr Gly Glu Thr Gly Gly Asn Ser Pro Val Gln Glu Phe Thr Val Pro
            165                 170                 175

Lys Asn Val Tyr Thr Ala Thr Ile Ser Gly Leu Lys Pro Gly Val Asp
            180                 185                 190

Tyr Thr Ile Thr Val Tyr Ala Val Thr Arg Phe Arg Asp Tyr Gln Pro
            195                 200                 205

Ile Ser Ile Asn Tyr Arg Thr Glu Ile Asp Lys Pro Cys Gln His His
            210                 215                 220

His His His His
225

<210> SEQ ID NO 2
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gly Val Ser Asp Val Pro Arg Asp Leu Glu Val Val Ala Ala Thr
1               5                   10                  15

Pro Thr Ser Leu Leu Ile Ser Trp Leu Pro Gly Lys Leu Arg Tyr Gln
                20                  25                  30

Tyr Tyr Arg Ile Thr Tyr Gly Glu Thr Gly Gly Asn Ser Pro Val Gln
            35                  40                  45

-continued

| | | | | | | | | | | | | |
|---|---|---|---|---|---|---|---|---|---|---|---|---|
| Glu | Phe 50 | Thr | Val | Pro | His 55 | Asp | Leu | Arg | Thr | Ala 60 | Thr | Ile | Ser | Gly | Leu |
| Lys 65 | Pro | Gly | Val | Asp | Tyr 70 | Thr | Ile | Thr | Val | Tyr 75 | Ala | Val | Thr | Asn | Met 80 |
| Met | His | Val | Glu | Tyr 85 | Ser | Glu | Tyr | Pro | Ile 90 | Ser | Ile | Asn | Tyr | Arg 95 | Thr |
| Glu | Ile | Asp | Lys 100 | Gly | Ser | Gly | Ser | Gly 105 | Ser | Gly | Ser | Gly | Ser 110 | Gly | Ser |
| Gly | Ser | Gly 115 | Ser | Gly | Ser | Gly | Ser 120 | Val | Ser | Asp | Val | Pro 125 | Arg | Asp | Leu |
| Glu | Val 130 | Val | Ala | Ala | Thr | Pro 135 | Thr | Ser | Leu | Leu | Ile 140 | Ser | Trp | Ser | Ala |
| Arg 145 | Leu | Lys | Val | Ala | Arg 150 | Tyr | Tyr | Arg | Ile | Thr 155 | Tyr | Gly | Glu | Thr | Gly 160 |
| Gly | Asn | Ser | Pro | Val 165 | Gln | Glu | Phe | Thr | Val 170 | Pro | Lys | Asn | Val | Tyr 175 | Thr |
| Ala | Thr | Ile | Ser 180 | Gly | Leu | Lys | Pro | Gly 185 | Val | Asp | Tyr | Thr | Ile 190 | Thr | Val |
| Tyr | Ala | Val 195 | Thr | Arg | Phe | Arg | Asp 200 | Tyr | Gln | Pro | Ile | Ser 205 | Ile | Asn | Tyr |
| Arg | Thr 210 | Glu | Ile | Asp | Lys | Pro 215 | Cys | Gln | His | His 220 | His | His | His | | |